(12) United States Patent
Davidson et al.

(10) Patent No.: US 6,601,456 B1
(45) Date of Patent: Aug. 5, 2003

(54) FRETTING FIXTURE FOR HIGH-CYCLE FATIGUE TEST MACHINES

(75) Inventors: David L. Davidson, San Antonio, TX (US); Thomas E. Owen, Helotes, TX (US); John B. Campbell, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 09/875,563

(22) Filed: Jun. 6, 2001

(51) Int. Cl.[7] .............................. G01N 3/00; G01N 3/32; G01N 3/56
(52) U.S. Cl. ............................ 73/808; 73/794; 73/83; 73/7
(58) Field of Search ...................... 73/808, 797, 794, 73/7, 83

(56) References Cited

U.S. PATENT DOCUMENTS

| | | | | |
|---|---|---|---|---|
| 2,872,805 A | * | 2/1959 | Cochran, Jr. et al. | 73/10 |
| 3,218,847 A | | 11/1965 | Starer et al. | 73/95 |
| 3,442,120 A | * | 5/1969 | Russenberger et al. | 73/577 |
| 4,567,774 A | * | 2/1986 | Manahan et al. | 374/49 |
| 4,637,259 A | * | 1/1987 | Jones | 73/794 |
| 4,869,111 A | * | 9/1989 | Ohya et al. | 73/811 |
| 4,869,112 A | * | 9/1989 | Gram et al. | 73/796 |
| 5,375,451 A | * | 12/1994 | Sandstrom | 73/577 |
| 5,581,040 A | * | 12/1996 | Lin | 73/883 |
| 5,677,494 A | * | 10/1997 | Keener et al. | 73/760 |
| 5,877,432 A | * | 3/1999 | Hartman et al. | 73/779 |
| 5,969,226 A | | 10/1999 | Wert et al. | 73/7 |
| 6,023,980 A | * | 2/2000 | Owen et al. | 73/797 |

FOREIGN PATENT DOCUMENTS

FR 2685773 A1 * 7/1993 ............. B06B/3/00

* cited by examiner

*Primary Examiner*—Hezron Williams
*Assistant Examiner*—Lilybett Martir
(74) *Attorney, Agent, or Firm*—Baker Botts L.L.P.

(57) ABSTRACT

A fretting fixture accessory for a test machine (10) that induces high-cycle fatigue (at kilohertz vibration rates) in a specimen of a material under test. The fretting fixture (20) is clamped to the test specimen (21), for the purpose of testing for fretting damage. The fixture (20) is designed to provide both the normal and shearing forces that result in fretting damage.

15 Claims, 4 Drawing Sheets

FRETTING FIXTURE FOR HIGH-CYCLE FATIGUE TEST MACHINES

GOVERNMENT RIGHTS

This invention was made with government support under government contract number F33615-96-C-5196 (SwRI Project No. 18-8653), with the U.S. Air Force, Air Force Research Laboratories, Ohio. The government has certain rights in the invention.

TECHNICAL FIELD OF THE INVENTION

The present invention relates generally to equipment for testing physical characteristics of materials, and more specifically, to a fretting fixture for a test machine that subjects a sample of material to high-cycle stress.

BACKGROUND OF THE INVENTION

One type of stress-related fatigue damage that may occur in materials is "fretting". It occurs on a load-bearing contact surface between two pieces of mating material. Conventional fatigue testing has been empirically based without providing quantitative experimental information on the forces that result in fretting.

U.S. Pat. No. 6,023,980, to Thomas E. Owen, et al., entitled "High-Cycle Fatigue Test Machine", describes a test machine that may be used to statically and dynamically load a test specimen in a manner that introduces controlled cyclic fatigue forces at high vibrational rates. A conventional use of this test machine is with a single specimen piece inserted between two actuators of the test machine, but this method of testing, by itself and without the supplemental fretting fixture invention described herein, does not introduce fretting forces in the specimen. However, by changing the method of excitation of this test machine, the static and dynamic forces applied to the specimen are modified and, additionally, the test specimen is made to undergo oscillatory translational motions along its length axis. As a result of these modified forces and translational motions and with the fretting fixture described herein attached to the specimen, the combined arrangement is capable of introducing fretting forces and fretting fatigue in the specimen.

The test machine described in U.S. Pat. No. 6,023,980 is recognized to have important advantages in imparting the desired controlled static and dynamic forces and translational motions to test specimens. However, by means of adaptations of the dynamic actuator component described in U.S. Pat. No. 6,023,980 in combination with the fretting fixture described herein, similar fretting testing results may be obtained using commercial materials testing machines capable of applying static tensile loading to the test specimen. In particular, a second test machine arrangement is one in which a specimen holder assembly and a dynamic actuator assembly are connected in tandem to form a tensile-loading column suitable for mounting in a conventional static-loading materials testing machine. When so mounted, the column may be placed in tension to produce a desired static tensile stress in the specimen. The dynamic actuator may then be excited to produce axially oriented mechanical vibration resonances in the column, with the principal resonance frequency governed by the compliance of the test specimen and combination of masses and compliances associated with the dynamic actuator assembly and the tensile-loading column components. When the dynamic actuator is caused to vibrate at the principal columnar resonance frequency, the specimen will undergo oscillatory translational motions. With the fretting fixture attached to the specimen, fretting fatigue effects may be induced in the specimen. The size and materials of the tensile-loading column and test specimen may be selected to cause principal mechanical resonances in the range of 1000–3000 Hz. The specimen holder assembly of this columnar testing module may be configured to accept the fretting fixture described herein without substantial modification.

SUMMARY OF THE INVENTION

One aspect of the invention is a fretting fixture for a test machine that induces high-cycle fatigue effects in prepared material test specimens. The test machine is assumed to be of a type that imparts both static tensile loading and dynamic oscillatory translational motions to a test specimen along its length axis. The fretting fixture is attached to the specimen and is freely supported on the specimen.

More specifically, the fretting fixture has a fretting piece that is placed against the test specimen. The combination of the fretting piece and the test specimen is positioned between two inertial masses comprising part of the fretting fixture and its clamping frame. That entire assembly is forcibly clamped onto and supported by the specimen.

An advantage of the invention is that it permits detailed and controlled study of material fretting effects during long-term cyclic vibration tests. Specifically, the fretting fixture permits accurate experimental simulation of fretting on material test specimens and accurate quantitative measurement of the applied static loading force and applied dynamic shear loading force that, in combination, induce the fretting effects. The forces are applied between two material surfaces, namely, the surface of the fretting piece and the surface of the test specimen, and are a result of oscillatory translation vibrations of the specimen at a frequency typically in the range of 1000–3000 Hz. The forces between the two surfaces are more clearly described as inertial reactions of the masses comprising part of the fretting fixture in response to the specimen oscillatory translation motions.

Another advantage of the invention is that the oscillatory translational displacement of the specimen relative to the fretting piece is measurable by means of sensors attached to the specimen grips and these motions may be controlled in amplitude by adjusting the excitation energy applied to the dynamic force actuators. The frequency of translational vibration and displacement can be made to be in the range of 1000–3000 Hz, depending on the physical design of the test machine, as in the case of the machine described in U.S. Pat. No. 6,023,980, or the design of the columnar testing module, as briefly described above, designed for use with commercial materials testing machines. This operating frequency range is a range in which fretting damage effects between mating materials are well known to occur. Likewise, force and acceleration sensors attached to the fretting fixture provide a quantitative measure of the fretting fixture static clamping force on the specimen and the dynamic reaction force between the fretting piece and the specimen.

DETAILED DESCRIPTION OF THE INVENTION

Figure 1:
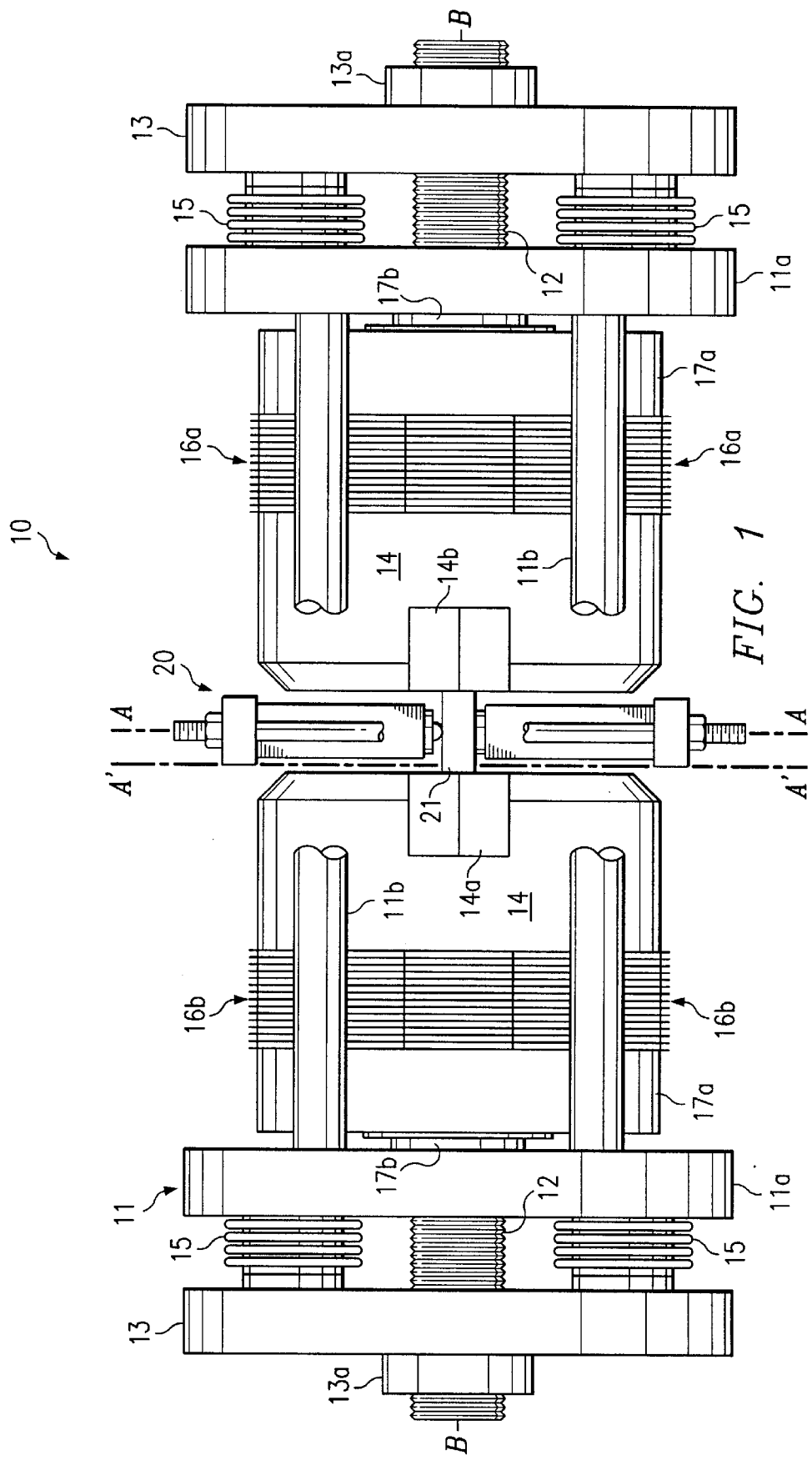
FIG. 1 illustrates a test machine having a fretting fixture in accordance with the invention.

The fretting fixture of the present invention is first described in detail by making specific reference to the test machine cited in U.S. Pat. No. 6,023,980 as illustrated in FIG. 1. A subsequent discussion, in reference to FIG. 5, describes how the fretting fixture operates with a commercial materials testing machine.

FIG. 1 illustrates a test machine 10 that is used to induce high-cycle fatigue in materials, and having a fretting fixture 20 in accordance with the present invention. Fretting fixture 20 is clamped to a specimen 21 in the manner described below in connection with FIGS. 2 and 3.

Test machine 10 is designed to subject a test specimen simultaneously to a static force and a cyclic dynamic force. The frequency range of the dynamic force typically can be 1,000 to 3,000 Hz, depending on the design of the test machine 10. Further details are described below, as well as in U.S. Pat. No. 6,023,980, referenced in the Background and incorporated by reference herein. That patent describes various embodiments of a high-cycle fatigue test machine, and test machine 10 is consistent with the principles and structure described therein.

More specifically, test machine 10 uses piezoelectrical means to activate the mechanical resonance of the specimen and test-machine combination. For inducing static loading conditions, test machine 10 uses hydraulic loading means. However, the invention is not limited to any particular configuration of a test machine, and could be used with any test machine 10 that receives a test specimen and that provides other means for applying appropriate static or dynamic loading. For example, as described in U.S. Pat. No. 6,023,980, pneumatic, piezoelectric, or electromechanical means could be used for static loading.

As stated above, test machine 10 is used for fatigue testing of prepared specimens made of selected materials to be subjected to stress testing. A particular type of stress, relevant to the present invention, is interface stress at surface-loaded contact points, such as between vibrating machine components. This stress can cause material fatigue. The initial damage that occurs as a result of this stress is referred to as "fretting" damage. If persistent, fretting can result in surface cracking and failure of the components involved. Fretting fixture 20 is used for inducing this type of damage, and is explained below in connection with FIGS. 2 and 3.

Test Machine Overview

Test machine 10 has various "structural elements", such as an inner reaction frame 11, which is comprised of end plates 11a and coupling rods 11b (typically four in number), and a stress transfer assembly, which is comprised of stress rods 12, bearing plates 13, and two coupling cylinders 14 containing specimen grips 14a and 14b, between which test specimen 21 is mounted. The "active" elements are two sets of bellows 15, which provide hydraulically induced static loading and a pair of piezoelectric actuators 16a and 16b, which provide dynamic loading. For purposes of describing the mechanical resonance frequency of a typical test machine 10, dimensions and other physical characteristics of these elements are described in U.S. Pat. No. 6,023,980.

Examples of suitable materials for constructing test machine 10 are iron, titanium, and aluminum alloys for the structural elements and piezoelectric ceramic for the piezoelectric actuators 16a and 16b. Although several specific materials are identified herein as being suitable and are used as examples, other materials are also suitable. For example, various iron alloys may be used to provide higher stresses or a smaller test machine. Also, the dynamic stresses may be produced by any one of several types of piezoelectric materials and ceramic compounds. Furthermore, the dynamic stresses may be produced by means of a magnetostrictive material, through appropriate modification of the dynamic loading actuators. In the case of a dynamic actuator made from magnetostrictive material, a set of rods with windings could be substituted for the piezoceramic stacks. These rods would be placed between the retaining plates 13 and the cylindrical couplers 14, parallel to the coupling rods 11b.

Test machine 10 is symmetrical with respect to cross-section A—A as indicated in FIG. 1. During normal high-cycle-fatigue testing without the use of fretting fixture 20, a stationary vibration node is located at the midpoint of test machine 10 along axis B—B. As a result of the symmetry of test machine 10, this vibration node is located at the midpoint of test specimen 21. This positioning ensures that maximum fatigue effects are induced in the central part of the specimen commonly referred to as the gauge section of the specimen. The various components of test machine 10, their symmetrical arrangement relative to cross-section A—A shown in FIG. 1, and the manner in which they contribute individually and collectively to the mechanical resonance of the specimen and test-machine combination are described in detail in U.S. Pat. No. 6,023,980.

Test Machine Operation to Produce Fretting Fatigue in the Test Specimen

For purposes of exciting fretting stresses in test specimen 21, the mode of operation of test machine 10, as described in U.S. Pat. No. 6,023,980, is made asymmetrical with respect to its physical center of mass. Such asymmetrical operation will produce translational motions of the specimen located under a fretting piece 24 that is part of fretting fixture 20, shown in FIG. 1.

The two piezoelectric actuators 16a and 16b of test machine 10 provide an effective means for shifting the resonance vibrations of test machine 10 from purely symmetrical about cross-section A—A shown in FIG. 1 to a combination of mechanical vibrations of the test machine that impart primarily oscillatory translation motions to test specimen 21 together with dynamic tension and compression forces in the test specimen. This desired result is achieved by reducing the electrical excitation applied to one piezoelectric actuator 16a while maintaining full excitation on the other piezoelectric actuator 16b. With a reduction in the excitation applied to the first actuator 16a, the vibration node originally located at the midpoint of specimen 21 is shifted away from that midpoint toward the end of specimen 21 nearest the fully excited actuator 16b, effectively moving the vibrational nodal point initially located at cross-section A—A away from the symmetrical center of mass of test machine 10 and relocating it at cross-section A'—A' as shown in FIG. 1; a position closer to the fully excited actuator 16b. The gauge section of specimen 21 on the opposite side of cross-section A'—A' from the fully excited actuator 16b therefore undergoes an increasing amount of oscillatory strain along its axis B—B as the excitation applied to the first actuator 16a is reduced. When observed from a hypothetically stationary observation point independent of test machine 10, the oscillatory strain motions can be recognized as oscillatory translation motions and, in particular, as oscillatory translation motions of the physical midpoint of specimen 21.

Fretting fixture 20 is clamped essentially at the physical midpoint of specimen 21, with fretting piece 24 in pressure contact with specimen 21 at its physical midpoint. Increasing or decreasing the excitation applied to the fully active actuator 16b has a directly proportional effect in changing the oscillatory displacement amplitude at the midpoint of test specimen 21.

Fretting Fixture for Test Machine

Figure 3:
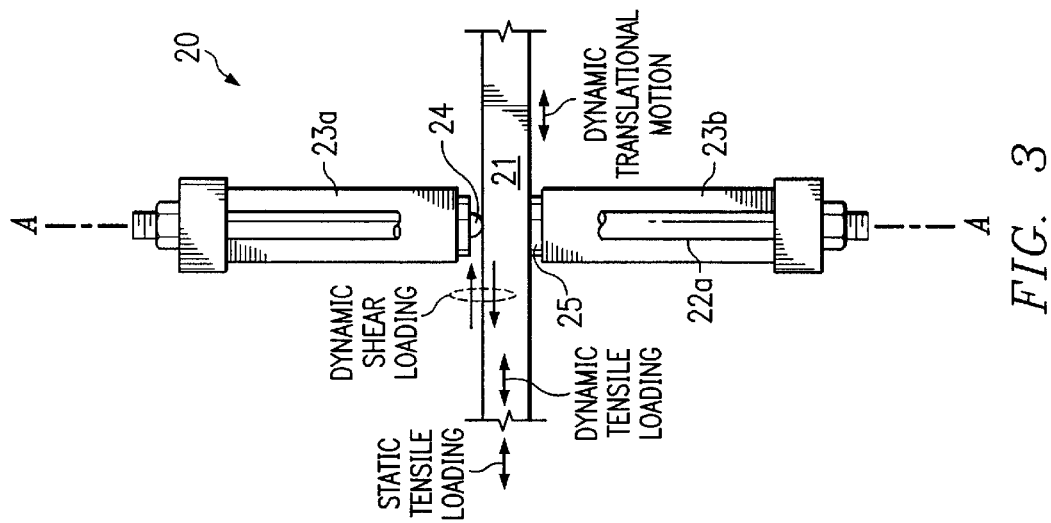
FIG. 3 is a side view of the fretting fixture.
Figure 2:
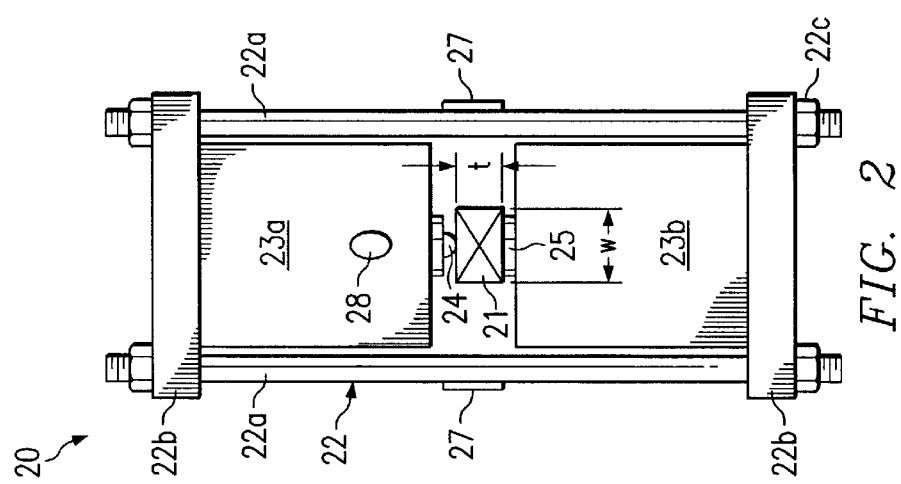
FIG. 2 illustrates the fretting fixture of FIG. 1.

FIGS. 2 and 3 are two views of fretting fixture 20. FIG. 2 is a front view along line A—A of FIG. 1, and FIG. 3 is a side view.

As stated above and as explained in additional detail below, with fretting fixture 20, test machine 10 makes possible the generation of the interface shear forces necessary for fretting fatigue testing. In particular, test machine 10 imparts to the test specimen, simultaneously, a static force and a dynamic force for controlled cyclic testing at vibrational rates in the frequency range of 1000–3000 Hz, depending on the test specimen size and material properties and the mass of the coupling cylinders 14 and other components of test machine 10. It may impose static tensile loading on the specimen at a force up to 6000 lbf and superimpose dynamic loading on the specimen at a double-amplitude oscillatory force up to 2400 lbf. Generation of the shear forces, through asymmetrical excitation, is made possible by the ability of test machine 10 to impart both a dynamic tensile loading vibration and a dynamic translational motion at the test machine mechanical resonance cyclic rate.

Fretting fixture 20 is essentially comprised of a clamping frame 22, two inertial masses 23a and 23b, and a fretting piece 24. The test specimen 21 and the fretting piece 24 are positioned between the inertial masses 23a and 23b, and the entire fretting fixture 20 is clamped onto specimen 21 by means of clamping frame 22.

Frame 22 has two or more loading rods 22a, with a clamping beam 22b at each end. The ends of rods 22a extend through holes in clamping beams 22b, and may be threaded. This permits nuts 22c to be used to clamp the specimen 21 and fretting piece 24, positioned between the inertial masses 23a and 23b, against each other within frame 22.

When nuts 22c are tightened, clamping frame 22 imparts an adjustable static loading force between fretting piece 24 and specimen 21. This static loading force is oriented normal to the surface of test specimen 21 and is an important quantitative parameter related to the interface stress conditions between fretting piece 24 and specimen 21 that result when specimen 21 undergoes oscillatory translation motion. Conventional strain gauge sensors 27 mounted on loading rods 22a are used to measure the normal force between the fretting piece and the specimen.

Inertial masses 23a and 23b are made from a high density material, such as a tungsten alloy. Masses 23a and 23b provide inertia for imparting the required shear force between specimen 21 and fretting piece 24. To achieve the transfer of the inertial reaction force of mass 23a to fretting piece 24 and thence to the contact point between the fretting piece 24 and the specimen 21, it should be understood that the inertial mass 23a and fretting piece 24 are rigidly attached together and thereby behave as a single combined mass. This inertial force, primarily imparted by mass 23a in reaction to the translation motions of specimen 21, is therefore the principal basis by which the shear forces and related fretting stresses are generated at the interface between the fretting piece and the specimen. The contact area between fretting piece 24 and specimen 21 is made sufficiently small to create compressional and shear forces of sufficient magnitude to cause fretting fatigue and subsequent fretting damage to the specimen as a result of long-duration cyclic testing. Mass 23b serves the function of providing a balancing inertial force, via a large-area non-fretting pad, on the opposite side of specimen 21 so that, in particular, the force between fretting piece 24 and specimen 21 is approximately a pure shear force at the fretting contact interface. The normal force imparted to fretting piece 24 at the shear-stressed interface is always adjusted to be at least sufficient but, in general, is made somewhat greater than necessary to prevent any sliding action between fretting piece 24 and specimen 21.

Fretting piece 24 may be, but need not necessarily be, made from the same material as specimen 21. In some cases, it may be made from the same material as a contacting material in a real-world environment. For example, where testing is being performed to determine the fretting effects of two contacting equipment parts, specimen 21 and fretting piece 24 may be made from the respective materials that are used for those parts.

Fretting piece 24 provides an area of contact onto specimen 21. This area of contact may be of a geometry (shape and size) that approximates the real-world equipment contact conditions being tested or, alternatively, it may be sized to impart stress levels necessary to validate a theoretical and/or numerical analysis of fretting fatigue in the test specimen material. For example, test machine 10 could be used to test fretting damage in a turbine engine by accurately simulating the contact conditions where a turbine blade is attached to a disk. This example may be extended to the case where special fretting piece contact geometries and applied fretting forces are used to establish the maximum operating forces that might exist in turbine blade assemblies before critical fretting damage begins to occur as an aid in developing predictive theories and methods for determining such material performance limits.

Specimen 21 has a sufficient length and mass and a suitable cross-section shape and surface condition relative to fretting piece 24 so as to provide a desired combination of shear and normal forces that will result in fretting. To this end, specimen 21 typically has a relatively long rectangular shape, being somewhat constrained in its other dimensions (thickness, T, and width, W) to allow the oscillatory longitudinal strains needed to produce the required translation motions of the test specimen as well as to provide a shape and length suitable for its placement within test machine 10 and supporting fretting fixture 20.

Fretting piece 24 has a material composition, a surface finish, a contact area, and a size and contour shape relative to specimen 21 that will result in fretting. Pad 25 acts as a counter-loading pad for the normal force that is applied to specimen 21 by clamping frame 20. Pad 25 is made from a non-fretting material such as a thin sheet of Teflon®.

The combination of the test specimen 21, inertial masses 23a and 23b, fretting piece 24, and pad 25 is assembled and held together by the clamping mechanism of frame 22. As explained above, test machine 10 is designed to hold specimen 21 in a space between coupling cylinders 14. Thus, test specimen 21 extends longitudinally between the coupling cylinders 14 of the test machine 10. The fretting device 20 is positioned at the midpoint of test specimen 21, such that it is perpendicular to the test specimen 21 and test machine axis B—B. In this arrangement, the loading rods 22a are perpendicular to the test specimen 21, while also being between the coupling cylinders 14.

As stated above, to accurately simulate the occurrence of fretting fatigue and damage, a proper combination of shear and normal forces must be applied at the specimen fretting contact area. As illustrated in FIG. 3, test machine 10 provides dynamic translation motion and provides both static and dynamic tensile loading of specimen 21. The contact area between specimen 21 and fretting piece 24 undergoes dynamic shear loading.

Conventional strain gauges (or load cells) 27 and accelerometer 28 mounted on inertial mass 23a may be used to measure the loading force conditions at the fretting contact area during fretting tests. These devices permit the shear and normal forces at the fretting contact to be measured and adjusted as may be necessary to provide the proper combination of forces for fretting. Specifically, strain gauges 27 measure the normal force, and accelerometer 28 measures the shearing force. Unlike other methods of fretting simulation, the static and dynamic forces associated with this fretting fixture 20 may be measured and known. Additional instrumentation associated with test machine 10 can be used to provide data on the oscillatory translational displacement motions of the test specimen, the cyclic vibrational frequency, and the accumulated number of vibration cycles during a given fretting test.

In general, simulation of fretting, as it may occur in a real-world environment, may require adjustment of a number of factors. As explained above, these factors include the shape and size of the fretting contact area, the mass, geometry, and composition of test specimen 21, and size of inertial masses 23a and 23b, as well as the magnitudes of the shear and normal forces applied at the fretting contact.

As illustrated in FIG. 3, the action of test machine 10 causes specimen 21 to stretch and compress along its longitudinal axis. A static normal force is supplied by the frame 22, which pushes the fretting piece 24 against the specimen 21. Surface stresses are produced by forces generated by the attached fretting test fixture 20 and, in particular, on fretting piece 24 as caused by inertial reaction of the inertial mass 23a. The resulting shear force is in response to the dynamic translational motion of the test specimen 21 to which the fretting fixture 20 is clamped. By making the fretting fixture 20 compact in size and high in mass, it represents a loading contact between the fretting piece 24 and the test specimen 21 such that fretting effects occur at a known and selected contact area. By making the fretting fixture 20 physically balanced and symmetrical with respect to the vibrational axis of the test specimen 21, through the use of inertial mass 23b and loading pad 25, extraneous vibrational modes (such as rocking motions at the fretting piece contact area) are avoided, thus providing well defined vibration conditions at the fretting contact position. Furthermore, by means of properly selected sensors and test machine materials, fretting testing can be performed at elevated temperatures as well as at ambient temperature.

Control System

Figure 4:
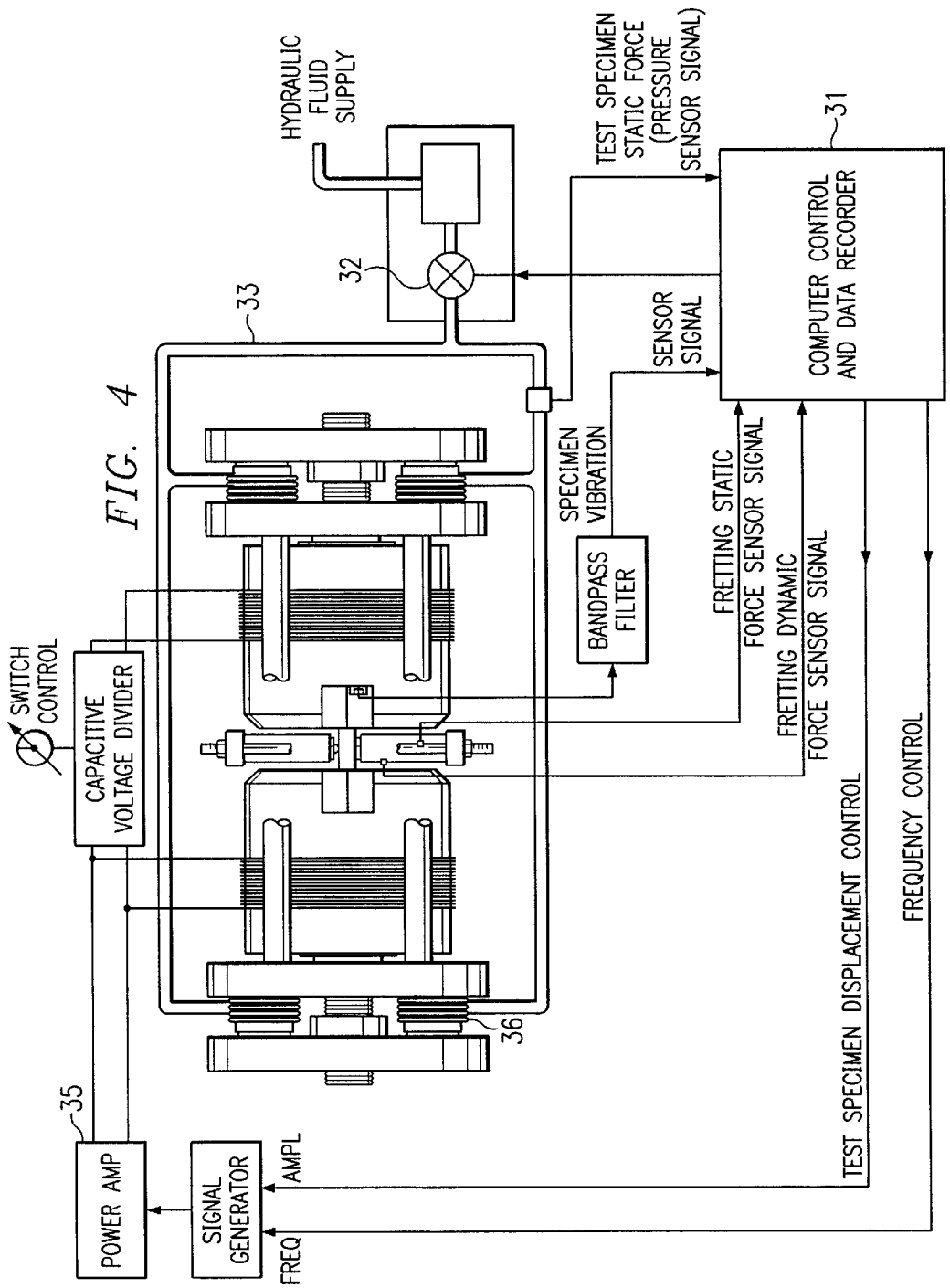
FIG. 4 illustrates the control system associated with the test machine and fretting fixture.

FIG. 4 illustrates a control system for test machine 10. A feature of the invention is that dynamic and static loading may be independently controlled. These forces may be maintained at preset values independent of the cyclic loading frequency.

As explained above, test machine 10 provides tensile static loading in combination with cyclic dynamic loading of test specimen 21. A computer 31 may be suitably programmed to handle control inputs for regulating both the static and dynamic stresses in the test specimen and its dynamic translational displacements as well as to record these and other test parameters. Computer 31 may be any general purpose personal or desktop computer, such as are commercially available. It may have appropriate interfaces for receiving input signals from strain gauges 27 and accelerometer 28, which are attached to fretting device 20.

Static loading of specimen 21 along axis B—B is controlled by adjusting the hydraulic pressure applied to test machine 10 via either a manually controlled or a computer controlled valve 32. Hydraulic fluid lines 33 carry hydraulic fluid to and from the bellows 15.

The dynamic excitation of the asymmetrical mechanical resonance vibrations of test machine 10 is produced by independently applying separate AC electrical excitation voltages to the piezoelectric actuators 16a and 16b. Vibrational forces generated by actuators 16a and 16b are transferred to the test specimen by means of the cylindrical couplers 14. A power amplifier 35 drives the two piezoelectric actuators 16a and 16b with actuator 16b receiving the full excitation voltage from power amplifier 35 and actuator 16a receiving its excitation voltage through a switch-adjustable capacitive voltage divider 36.

The operating mechanical resonance frequency of test machine 10 is primarily a function of the stiffness (effective rod-type spring constant) of test specimen 21 in combination with the masses of the cylindrical couplers 14 attached to the specimen via specimen grips 14a and 14b identified in FIG. 1. The effective stiffness of specimen 21 will depend upon the specific test specimen geometry and material composition and can be expected to change with temperature and with the fatigue status of the specimen as it may develop during the cyclic testing. Such variations in resonance can present a problem in maintaining uniform stress excitation and translation motions in the specimen during the fatigue testing cycle since the frequency of the excitation voltage must always be tuned to the mechanical resonance frequency to maintain uniform oscillatory forces and motions of the specimen throughout the test. Without a knowledge of the prevailing mechanical resonance frequency of the test machine system and a capability for adjusting the excitation frequency and amplitude to match the test machine resonance frequency and the desired preset level of oscillatory forces and translation motions, the fretting test conditions and specimen fretting fatigue effects may not be accurately realized. For this reason, a vibration sensor 36 is used to sense the dynamic resonance frequency and amplitude of test machine and fretting fixture vibrations during testing. This sensor signal is coupled to computer 31 where it is automatically measured in frequency and amplitude and, if needed, a frequency adjustment control signal and/or an amplitude control signal, is generated and delivered to the excitation signal generator to accurately track any changes in test machine operation. This arrangement ensures that the fretting fatigue stresses in the specimen, governed primarily by the vibrational energy of the fretting fixture 20, will be maintained constant throughout the test period. Such automatic machine control by computer 31 also frees the system operator from having to perform the excitation measurements and adjustments manually during the usually lengthy high-cycle fatigue tests.

By means of vibration sensor 37, a signal directly proportional to the cyclic loading force on the specimen 21 and the frequency of oscillation of test machine 10 is obtained. This signal is filtered by bandpass filter 38 to remove any harmonic distortion and is fed to the computer 31. Computer 31 is programmed to periodically apply an analyzing algorithm to the filtered sensor signal and, as a result of this analysis, deliver controlling adjustments to the excitation signal generator 39 and power amplifier 35 to produce the desired amplitude of sinusoidal cyclic stress applied to the specimen, independently of the machine mechanical resonance frequency. This form of computer-automated periodic analysis and control of the power amplifier 35 output voltages applied to actuators 16a and 16b ensures that the electrical drive signals always satisfy the desired mechanical resonance excitation of test machine 10 and the preset stress conditions intended for the fretting tests, thereby tracking any changes in resonance that may occur due to changes in temperature or specimen physical properties.

The static loading imparted to the test specimen by test machine 10 is also controlled at a preset value by sensing the hydraulic fluid pressure in the bellows pressurizing system by pressure sensor 40 and regulating the applied pressure by adjusting valve 32. Valve 32 may be controlled automatically by computer 31, via the pressure signal derived from sensor 40, to achieve automatic operation of the overall testing system and to provide a means for safety shutdown of the bellows pressurizing system in the event that a specimen failure or other malfunction of the system might occur.

Columnar Assembly for Use with Other Testing Machines

Figure 5:
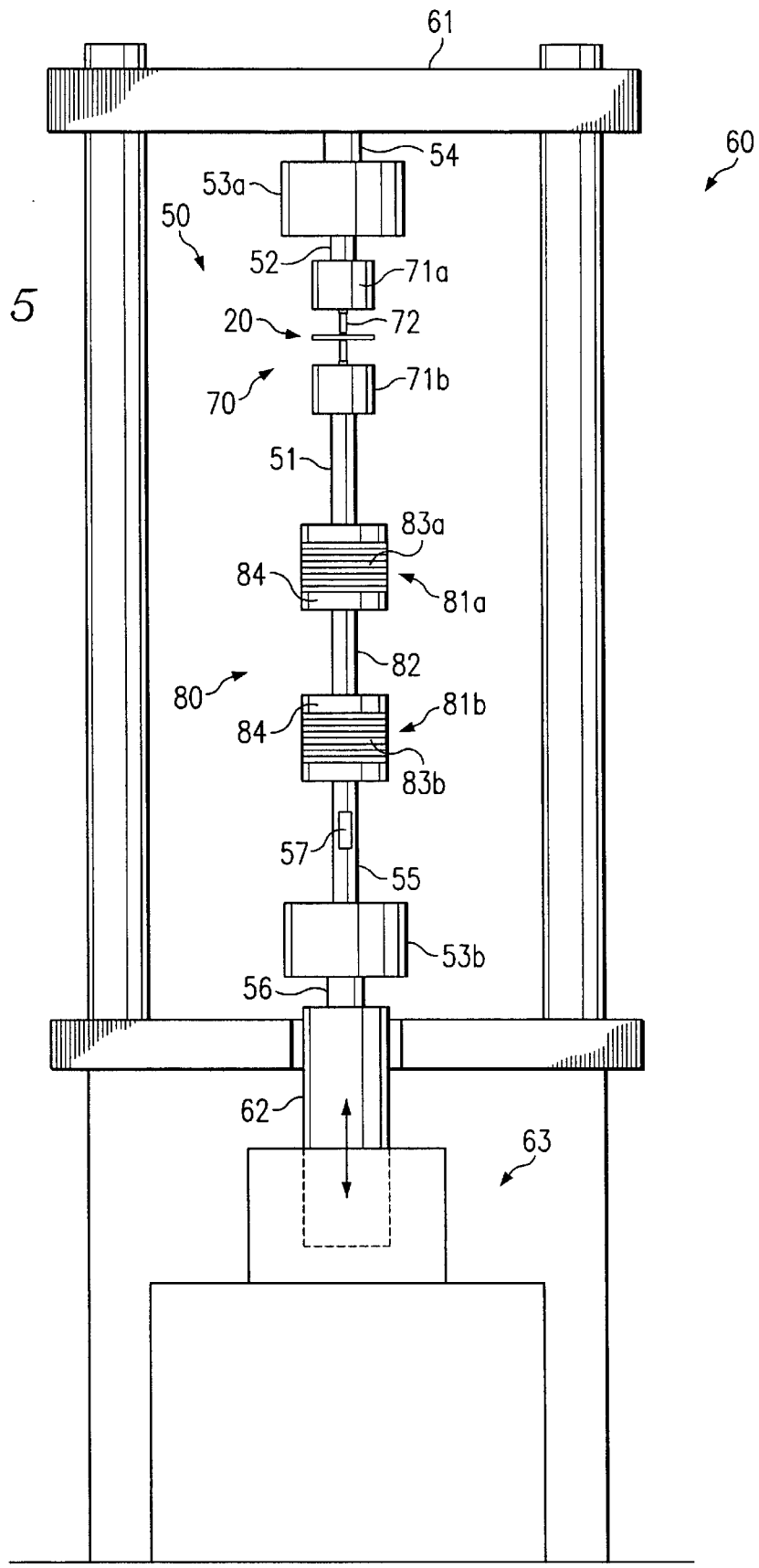
FIG. 5 illustrates a columnar testing module having a fretting fixture in accordance with the invention.

FIG. 5 illustrates a columnar testing assembly 50 for producing fretting fatigue in test specimens when operated in conjunction with a commercial materials testing machine 60 capable of producing an appropriate static tensile loading force on the specimen. Column assembly 50 consists of a specimen holder unit 70 comprised of two specimen grips 71a and 71b holding the ends of a test specimen 72, and a dynamic actuator unit 80 comprised of two piezoelectric actuators 81a and 81b joined together by a compliant coupling bar 82. One end of the specimen holder unit 70, for example, the grip component 71b, is attached to one end of the dynamic actuator unit 80, for example, actuator 81a, by a stiff coupling rod 51. Vibrations of dynamic actuator unit 80 are transferred to the specimen holder unit 70 and, in turn, to the test specimen 72 by the coupling rod 51. The opposite (upper) end of specimen holder unit 70, for example, grip component 71a, is attached to a vibration isolation mass 53a by a stiff coupling rod 52 and isolation mass 53a, in turn, is attached to the stationary top beam 61 of test machine 60 by a stiff coupling rod 54. The opposite (lower) end of the dynamic actuator unit 80, for example, actuator 81b, is attached to a second isolation mass 53b by a stiff coupling rod 55. The isolation mass 53b is attached to the moveable head 62 of the of test machine 60 by a stiff coupling rod 56. The active mechanism 63 of test machine 60 imparts a tensile loading force on column assembly 50 such that all of the components comprising column assembly 50 are subject to the same tensile loading force.

The active mechanism 63 of test machine 60 may utilize any one of several operating methods, such as hydraulic, electromechanical, or servo-electric, to apply static mechanical tension to the column assembly 50. Downward movement of the moveable head 62 shown in FIG. 5 will apply a tensile force to column assembly 50. Most commercial testing machines appropriate for use in this intended application have built-in load cells or calibrated strain gauges by which the tensile loading force is sensed and displayed to the operator. Further, many such test machines have an input/output signal and command and control interface by which the machine may be controlled by external means. Additionally, at least one strain gauge, shown in one place by item 57 in FIG. 5, may be mounted on any of the coupling rods 51, 52, or 55 or on the test specimen 72 to measure the static tensile force on the column assembly 50 which, correspondingly, is the same as the static tensile force on the test specimen 72.

The function of isolation masses 53a and 53b is to prevent the vibrations of the column assembly 50 from being transferred to the top beam 61 and to the moveable head 62 of test machine 60 and, in turn, to prevent any of the structural elements of test machine 60 from having an effect on the mechanical resonance behavior of the column assembly 50. By making each of the isolation masses approximately one order of magnitude greater than the mass of the dynamic actuator unit 80, only minor and negligible dynamic displacements of isolation masses 53a and 53b will occur.

The piezoelectric actuator stacks 83a and 83b and the cylindrical couplers 84 in dynamic actuator 80 are typically similar to those described earlier under Test Machine Review and, in particular, refer to items 16a and 16b and 14, respectively, in FIG. 1. Likewise, the compliant bar 82 of FIG. 5 is assembled in place of items 21 and 14a and 14b of FIG. 1. By means of this revised actuator configuration, the entire combination of components comprising the column assembly 50 between isolation masses 53a and 53b may be caused to vibrate and thereby superimpose oscillatory dynamic forces onto the tensile forces already present in the column assembly 50. Under this dynamic operating condition, if the frequency of the AC electrical excitation voltage applied to piezoelectric actuator stacks 83a and 83b is varied from a low value to a high value, several mechanical resonances will occur in the column assembly 50. Each successive resonance will be associated with a specific effective combination of compliances and masses comprising the frequency-dependent complex mechanical impedance of the column. In particular, since the coupling bar 82 and the coupling rods 51, 52, and 55, all of which are subject to strong dynamic vibrations, are all deliberately made stiffer than the test specimen 72, the lowest mechanical resonance of column assembly 50 will be governed primarily by the compliance of the test specimen 72 and an effective dynamic equivalent mass representing the net mechanical impedance of the other components of column assembly 50 at the particular resonance governed by specimen 72. Furthermore, when considered separately, the mechanical resonance frequency of the dynamic actuator unit 80 will be at a higher frequency than the specimen resonance frequency and will be governed primarily by the compliance of the coupling bar 82 and the masses of the attached actuator components 83a and 83b and 84 in combination with secondary effects introduced by the other components in the column assembly 50.

In order to excite the desired mechanical resonance governed by the test specimen, the electrical polarities of the AC voltages applied to piezoelectric actuator stacks 83a and 83b are such that the two stacks simultaneously and synchronously push and pull on coupling bar 82 and, thus, as a combined unit, dynamic actuator 80 also simultaneously and synchronously pulls and pushes on coupling rods 51 and 55 to introduce a strong dynamic force into those coupling rods 51 and 55 and into specimen holder 70. Moreover, since the test specimen 72 is the most compliant component in the column assembly 50, it will experience the largest dynamic strain of all elements of the column and this strain will have a maximum amplitude when the frequency of electrical excitation applied to dynamic actuator unit 80 corresponds to the mechanical resonance frequency determined by the compliance of test specimen 72.

Fretting Fixture Operation as Part of the Column Assembly

In the mode of operation described above, the lower end of test specimen 72, shown in FIG. 5, will undergo a substantial oscillatory translational displacement relative to its upper end. This dynamic displacement is the desired mechanical condition for applying the fretting fixture 20, described earlier under Fretting Fixture for Test Machine and illustrated in FIGS. 2 and 3, to the test specimen. For this purpose, the fretting fixture 20 is attached to test specimen 72 in the same manner discussed earlier, namely, by clamping it at the midpoint of specimen 72 such that it is freely supported by the specimen 72. This clamping action places the fretting piece 24, also shown in FIGS. 2 and 3, in pressure contact with specimen 72 to provide a desired and measurable normal force at the point of contact. When the dynamic actuator unit 80 of the column assembly 50 is excited at the mechanical resonance governed by the test specimen, that is, at the principal resonance of column assembly 50, the test specimen 72 undergoes oscillatory translational motions and, thereby, causes a dynamic shear force to be produced at the point of contact of fretting piece 24 and specimen 72. This dynamic shear force is measurable by acceleration sensor 28 attached to inertial mass 23*a*, shown in FIG. 2.

By selecting the size and materials of the components comprising the column assembly 50, the mechanical resonance frequency of the column system may be adjusted to fall in the general range of about 1000–3000 Hz, depending on the physical characteristics of specimen 72. For example, one convenient method of adjusting this principal resonance is to make the coupling rod 55 from stainless steel and to make its length and/or diameter such that the desired resonance frequency is achieved. Both of the dimensional parameters mentioned affect the mechanical stiffness of the rod, and this stiffness, in turn, has a direct effect on the net complex mechanical impedance of the column assembly 50, and thereby a corresponding effect on the principal resonance frequency. Thus, by experimentally modifying coupling rod 55, the principal resonance of the column assembly 50 may be adjusted to a desired value for conducting fretting fatigue tests. In particular, lengthening or reducing the diameter of coupling rod 55 will shift the principal resonance down in frequency whereas making the length shorter or the diameter larger will shift the principal resonance up in frequency.

The fretting fixture testing system illustrated in FIG. 5 includes sensor components attached to both the fretting fixture 20 and, for example, to the specimen holder grip component 71*b* to provide quantitative measurements and signals to indicate the normal compressional force and dynamic shear force at the contact point between fretting piece 24 and specimen 72 as well as the oscillatory translational displacement of the end of the gauge section of specimen 72 held in grip component 71*b*. This latter signal also contains information on the amplitude and frequency of the mechanical resonance as governed by the test specimen 72. In addition to these dynamic sensor signals, the static tensile force is obtained either as a signal from a strain gauge attached to column assembly 50, for example, on coupling rod 55, or directly as a readout from the test machine 60.

Computer control of the dynamic actuator unit 80 and the test machine 60 may be achieved as described earlier in the Section entitled "Control System", by tracking the mechanical resonance frequency of the column assembly 50 and adjusting the amplitude and frequency of the exciter signal by means of control commands fed to a programmable signal generator 39 which, in turn, adjusts the excitation signal applied to the power amplifier 35. The static tensile load applied to the test specimen 72 may be controlled by command signals delivered to the control mechanism 63 of test machine 60 provided that such a control capability is available as part of test machine 60.

Other Embodiments

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A fretting fixture for attachment to a specimen mounted in a fatigue testing machine, comprising:

a clamping frame having at least two loading rods and two clamping beams, such that each loading rod extends through a clamping beam at each end;

a pair of inertial masses inside said clamping frame, one adjacent to each clamping beam such that an air gap exists between opposing surfaces of the inertial masses within the frame; and a fretting contact piece attached to at least one of the opposing surfaces;

the clamping frame operable to clamp the inertial masses to the specimen, one on each side of the specimen, with the fretting contact piece between one of the inertial masses and the specimen, such that the fretting fixture is supported by the specimen and moveable in space with the specimen.

2. The fretting fixture of claim 1, further comprising at least one accelerometer attached to the fretting fixture.

3. The fretting fixture of claim 1, further comprising at least one strain gauge attached to the fretting fixture.

4. The fretting fixture of claim 1, wherein the inertial masses are made at least primarily of a high density material.

5. A method of testing, for fretting stress, a specimen already mounted in a test machine, comprising the steps of:

placing a fretting piece against the test specimen, the fretting piece having a contact area on a surface of the test specimen;

clamping an inertial mass on each side of the combination of the test specimen and the fretting piece, thereby resulting in a fretting fixture assembly of the inertial masses clamped to the specimen, one on each side of the specimen, with the fretting contact piece between one of the inertial masses and the specimen, such that the fretting fixture is supported by the specimen and moveable in space with the specimen; and activating the test machine thereby causing the test specimen and fretting fixture to oscillate.

6. The method of claim 5, further comprising the step of using the test machine to apply a static load on the test specimen.

7. The method of claim 6, wherein the test specimen is placed inside a test machine frame, and step of applying a static load is performed with force applied to the frame.

8. The method of claim 6, wherein said step of applying a static load places said test specimen in tension.

9. The method of claim 5, further comprising the step of using the test machine to apply a dynamic load on the test specimen.

10. The method of claim 9, wherein the dynamic load is applied with one or more dynamic actuators.

11. The method of claim 5, wherein said test specimen oscillations are translation motions along its length axis.

12. The method of claim 5, further comprising the step of placing a nonfretting contact pad on the opposite side of said test specimen in contact with the fretting piece between one of the inertial masses and the specimen.

13. The method of claim 5, wherein the clamping step is performed by placing a clamping frame around the assembly comprised of the inertial masses, the test specimen, and the fretting piece.

14. The method of claim 5, wherein the said test specimen has a lengthwise vibrational axis and wherein the said fretting fixture is oriented normal to the vibrational axis with said fretting piece positioned and clamped at the midpoint of the test specimen.

15. The method of claim 5, wherein said clamping frame used in said clamping step has sensing means for determining the clamping force and the shear force at the contact between said fretting piece and said test specimen.

* * * * *

UNITED STATES PATENT AND TRADEMARK OFFICE
CERTIFICATE OF CORRECTION

PATENT NO. : 6,601,456 B1
DATED : August 5, 2003
INVENTOR(S) : Davidson et al.

It is certified that error appears in the above-identified patent and that said Letters Patent is hereby corrected as shown below:

Underline Column 1,
Line 7, please delete "F33615-96-C-5196" and replace with -- F33615-96-C-5269 --.

Signed and Sealed this

Twentieth Day of January, 2004

JON W. DUDAS
*Acting Director of the United States Patent and Trademark Office*